(12) United States Patent
Johnston et al.

(10) Patent No.: US 12,350,030 B2
(45) Date of Patent: *Jul. 8, 2025

(54) EVENT DETECTION IN AN IMPLANTABLE AUDITORY PROSTHESIS

(71) Applicant: Cochlear Limited, Macquarie University (AU)

(72) Inventors: Benjamin Peter Johnston, Wollstonecraft (AU); Paul Michael Carter, West Pennant Hills (AU); Stuart John Kay, Marsfield (AU); Andrea Lam, Ryde (AU); Shaun Ashwin Kumar, Rockdale (AU); Joerg Pesch, Mechelen (BE)

(73) Assignee: Cochlear Limited, Macquarie University (AU)

( * ) Notice: Subject to any disclaimer, the term of this patent is extended or adjusted under 35 U.S.C. 154(b) by 239 days.

This patent is subject to a terminal disclaimer.

(21) Appl. No.: 17/956,189

(22) Filed: Sep. 29, 2022

(65) Prior Publication Data

US 2023/0100626 A1 Mar. 30, 2023

Related U.S. Application Data

(63) Continuation of application No. 16/725,434, filed on Dec. 23, 2019, now Pat. No. 11,484,218, which is a
(Continued)

(51) Int. Cl.
*A61B 5/053* (2021.01)
*A61B 5/00* (2006.01)
(Continued)

(52) U.S. Cl.
CPC ............ *A61B 5/053* (2013.01); *A61B 5/7282* (2013.01); *A61B 2505/05* (2013.01);
(Continued)

(58) Field of Classification Search
CPC ... A61B 5/053; A61B 5/7282; A61B 2505/05; A61N 1/0529; A61N 1/0541; A61N 1/36038
See application file for complete search history.

(56) References Cited

U.S. PATENT DOCUMENTS 4,990,845 A 2/1991 Gord
5,626,629 A 5/1997 Faltys et al.
(Continued)

FOREIGN PATENT DOCUMENTS

| | | |
|---|---|---|
| CN | 103815988 A | 5/2014 |
| WO | 2013/152077 A1 | 10/2013 |
| WO | 2015/168388 A1 | 11/2015 |

OTHER PUBLICATIONS

Communication pursuant to Article 94(3) in counterpart European Application No. 15 837 396.9-1122, mailed Nov. 6, 2024, 6 pages.
(Continued)

*Primary Examiner* — Christopher A Flory
(74) *Attorney, Agent, or Firm* — Edell, Shapiro & Finnan, LLC

(57) ABSTRACT

Presented herein are techniques for monitoring the physical state of a stimulating assembly to, for example, detect the occurrence of an adverse event. More specifically, an elongate stimulating assembly comprising a plurality of longitudinally spaced contacts is at least partially implanted into a recipient. Electrical measurements are performed at one or more of the plurality of contacts and the electrical measurements are evaluated relative to one another to determine the physical state of the stimulating assembly.

24 Claims, 11 Drawing Sheets

Related U.S. Application Data continuation of application No. 15/679,644, filed on Aug. 17, 2017, now Pat. No. 10,549,094, which is a continuation of application No. 14/843,255, filed on Sep. 2, 2015, now abandoned.

(60) Provisional application No. 62/044,595, filed on Sep. 2, 2014.

(51) Int. Cl.
 *A61N 1/05* (2006.01)
 *A61N 1/36* (2006.01)
(52) U.S. Cl.
 CPC .......... *A61N 1/0529* (2013.01); *A61N 1/0541* (2013.01); *A61N 1/36038* (2017.08)

(56) References Cited

U.S. PATENT DOCUMENTS

| | | | |
|---|---|---|---|
| 6,068,652 A | 5/2000 | Cohen et al. | |
| 8,073,547 B2 | 12/2011 | Hong et al. | |
| 8,401,665 B2 | 3/2013 | Bradley et al. | |
| 8,498,699 B2 | 7/2013 | Wells et al. | |
| 8,532,781 B1 | 9/2013 | Vanpoucke | |
| 8,554,330 B2 | 10/2013 | Bradley et al. | |
| 8,594,799 B2 | 11/2013 | Haller et al. | |
| 8,644,944 B2* | 2/2014 | Capcelea | H04R 25/554 607/57 |
| 8,788,057 B2 | 7/2014 | Stevenson | |
| 9,242,067 B2 | 1/2016 | Shore et al. | |
| 9,320,887 B2 | 4/2016 | Kals | |
| 10,099,054 B2 | 10/2018 | Laudanski | |
| 10,278,610 B2 | 5/2019 | Tsampazis | |
| 2005/0015133 A1 | 1/2005 | Ibrahim et al. | |
| 2006/0025833 A1 | 2/2006 | Daly | |
| 2006/0149337 A1 | 7/2006 | John | |
| 2006/0217782 A1 | 9/2006 | Boveja et al. | |
| 2006/0247684 A1 | 11/2006 | Halperin | |
| 2008/0125833 A1 | 5/2008 | Bradley et al. | |
| 2009/0030485 A1 | 1/2009 | Mishra et al. | |
| 2009/0118795 A1 | 5/2009 | Ibrahim et al. | |
| 2009/0312817 A1 | 12/2009 | Hogle et al. | |
| 2010/0106232 A1 | 4/2010 | Dadd et al. | |
| 2010/0114288 A1 | 5/2010 | Heller | |
| 2010/0198301 A1 | 8/2010 | Smith | |
| 2010/0222857 A1 | 9/2010 | Halperin et al. | |
| 2010/0268302 A1 | 10/2010 | Botros | |
| 2010/0292759 A1 | 11/2010 | Hahn et al. | |
| 2010/0324639 A1 | 12/2010 | Stevenson et al. | |
| 2011/0022140 A1 | 1/2011 | Stevenson et al. | |
| 2011/0066160 A1 | 3/2011 | Simaan et al. | |
| 2011/0087085 A1 | 4/2011 | Tsampazis et al. | |
| 2011/0106101 A1 | 5/2011 | Tortonese et al. | |
| 2011/0144719 A1 | 6/2011 | Perkins et al. | |
| 2011/0166627 A1* | 7/2011 | Carter | A61N 1/0541 607/57 |
| 2011/0201944 A1 | 8/2011 | Higgins et al. | |
| 2011/0213444 A1 | 9/2011 | Stoffaneller et al. | |
| 2011/0245714 A1 | 10/2011 | Volckaerts | |
| 2011/0264155 A1 | 10/2011 | Van den Heuvel et al. | |
| 2011/0306860 A1 | 12/2011 | Halperin et al. | |
| 2012/0029593 A1 | 2/2012 | Calle et al. | |
| 2012/0065705 A1 | 3/2012 | Kats | |
| 2012/0071956 A1 | 3/2012 | Stevenson et al. | |
| 2012/0078319 A1 | 3/2012 | De Ridder | |
| 2012/0109274 A1 | 5/2012 | Simaan et al. | |
| 2012/0143284 A1 | 6/2012 | Capcelea | |
| 2012/0188027 A1 | 7/2012 | Halperin et al. | |
| 2012/0226200 A1 | 9/2012 | Wagner et al. | |
| 2012/0226332 A1 | 9/2012 | Chambers et al. | |
| 2012/0245666 A1 | 9/2012 | Jolly et al. | |
| 2012/0316454 A1 | 12/2012 | Carter | |
| 2013/0073021 A1 | 3/2013 | Halperin et al. | |
| 2013/0138117 A1 | 5/2013 | Abbott et al. | |
| 2013/0204326 A1 | 8/2013 | Vanpoucke | |
| 2013/0253297 A1 | 9/2013 | Johnson et al. | |
| 2013/0331779 A1 | 12/2013 | Dhanasingh et al. | |
| 2014/0012351 A1 | 1/2014 | Calle et al. | |
| 2014/0046402 A1 | 2/2014 | Saoji | |
| 2014/0058478 A1 | 2/2014 | Fruhauf et al. | |
| 2014/0288619 A1 | 9/2014 | Johnson et al. | |
| 2014/0330345 A1 | 11/2014 | John | |
| 2014/0350640 A1 | 11/2014 | Patrick et al. | |
| 2015/0005845 A1 | 1/2015 | Fruhauf et al. | |
| 2015/0018897 A1 | 1/2015 | Laudanski | |
| 2015/0066107 A1 | 3/2015 | Richter et al. | |
| 2015/0088212 A1 | 3/2015 | De Ridder | |
| 2015/0112408 A1 | 4/2015 | Kals | |
| 2015/0207484 A1 | 7/2015 | Stevenson et al. | |
| 2015/0224313 A1 | 8/2015 | Smith et al. | |
| 2015/0258337 A1 | 9/2015 | Long | |
| 2015/0290453 A1 | 10/2015 | Tyler et al. | |
| 2015/0314122 A1 | 11/2015 | Kabot et al. | |
| 2015/0335890 A1 | 11/2015 | Fredelake et al. | |
| 2016/0015291 A1 | 1/2016 | Tsampazis | |
| 2016/0038738 A1 | 2/2016 | Naylor | |
| 2016/0059014 A1 | 3/2016 | Johnston et al. | |
| 2016/0059015 A1 | 3/2016 | Risi et al. | |
| 2016/0199648 A1 | 7/2016 | Richter et al. | |
| 2018/0304076 A1* | 10/2018 | Lehmann | A61N 1/025 |

OTHER PUBLICATIONS

Vanpoucke et al., Assessing the Placement of a Cochlear Electrode Array by Multidimensional Scaling, IEEE Transactions on Biomedical Engineering, vol. 59, No. 2, Feb. 12, pp. 307-310.

B. Escudé et al., "The Size of the Cochlea and Predictions of Insertion Depth Angles for Cochlear Implant Electrodes", Audiology & Neurotology, www.karger.com/aud, Audiol Neurotol 2006; 11 (suppl 1):27-33, DOI: 10.1159/000095611, Published online Oct. 6, 2006, 7 pages.

International Search Report and Written Opinion in counterpart International Application No. PCT/IB2015/056667, mailed Dec. 17, 2015, 10 pages.

\* cited by examiner

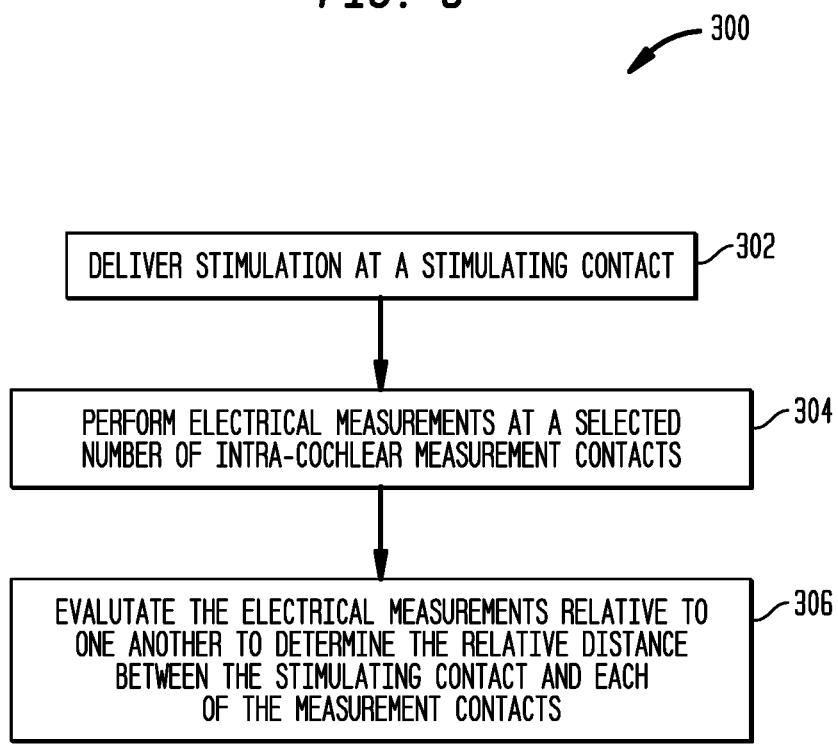

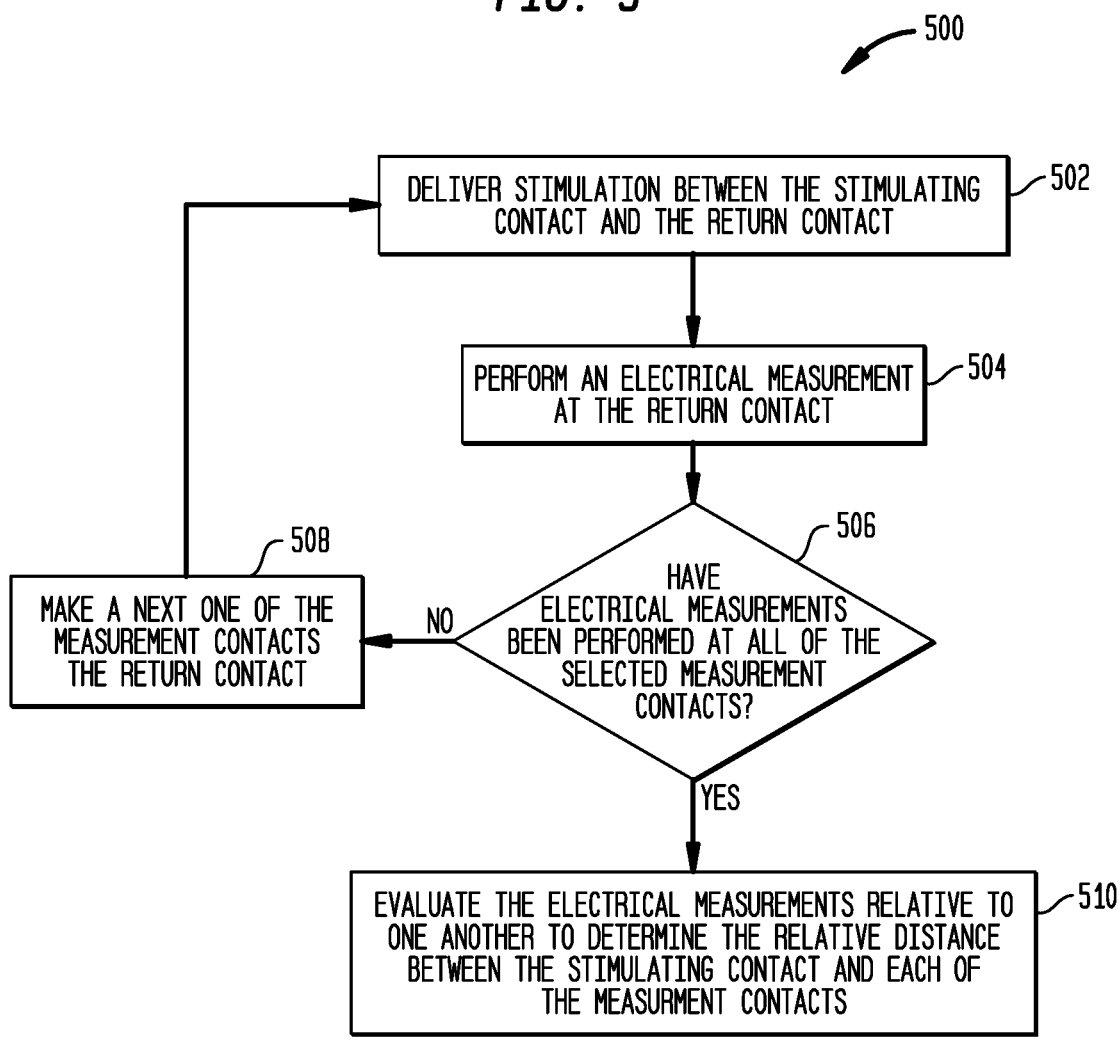

EVENT DETECTION IN AN IMPLANTABLE AUDITORY PROSTHESIS

CROSS-REFERENCE TO RELATED APPLICATIONS

This application is a continuation application of U.S. patent application Ser. No. 16/725,434, filed Dec. 23, 2019, which is a continuation application of U.S. patent application Ser. No. 15/679,644, filed on Aug. 17, 2017, now U.S. Pat. No. 10,549,094, issued Feb. 4, 2020, which is a continuation application of U.S. patent application Ser. No. 14/843,255, filed on Sep. 2, 2015, which in turn claims priority to U.S. Provisional Application No. 62/044,595, entitled "Event Detection in an Implantable Auditory Prosthesis", filed Sep. 2, 2014. The content of these applications are hereby incorporated by reference herein.

FIELD OF THE INVENTION

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

SUMMARY

In one aspect of the invention, a system is provided. The system comprises an elongate stimulating assembly configured to be implanted in a recipient, wherein the stimulating assembly comprises a plurality of longitudinally spaced contacts, and an event detection processor configured to utilize variations in electrical measurements between two or more contacts to determine a physical state of the stimulating assembly.

In another aspect of the invention, a method for monitoring an implantable stimulating assembly comprising a plurality of longitudinally spaced contacts is provided. The method comprises delivering electrical stimulation between two or more of the contacts, measuring electrical parameters at a selected number of the plurality of contacts in response to the delivered electrical stimulation, and evaluating the measured electrical parameters relative to one another to determine a physical state of the stimulating assembly.

In another aspect of the invention, one or more non-transitory computer readable storage devices encoded with software comprising computer executable instructions for monitoring an implantable stimulating assembly comprising a plurality of longitudinally spaced contacts are provided. When the software is executed, the software is operable to deliver electrical stimulation between two or more of the contacts, measure electrical parameters at a selected number of the plurality of contacts in response to the delivered electrical stimulation, and evaluate the measured electrical parameters relative to one another to determine a physical state of the stimulating assembly.

In another aspect of the invention, a cochlear implant system is provided. The cochlear implant system comprises an intra-cochlear stimulating assembly comprising a plurality of contacts and configured to deliver electrical stimulation between two or more of contacts, an implantable stimulator unit, and a processor. The processor is configured to measure, via the implantable stimulator unit, electrical parameters at a selected number of the plurality of contacts in response to the delivered electrical stimulation, and evaluate the measured electrical parameters relative to one another to determine a physical state of the stimulating assembly.

BRIEF DESCRIPTION OF THE DRAWINGS

Embodiments of the present invention are described herein in conjunction with the accompanying drawings, in which:

FIG. 3 is a flowchart of a localized monitoring method in accordance with embodiments presented herein;

FIG. 5 is a flowchart of a bipolar monitoring method in accordance with embodiments presented herein;

DETAILED DESCRIPTION

Presented herein are techniques for monitoring the physical state of a stimulating assembly to, for example, detect the occurrence of an adverse event. More specifically, an elongate stimulating assembly comprising a plurality of longitudinally spaced contacts is at least partially implanted into a recipient. Electrical measurements are performed at one or more of the plurality of contacts and the electrical measurements are evaluated relative to one another to determine the physical state of the stimulating assembly.

There are different types of auditory prostheses that may be partially or fully implanted into a recipient, including electrically stimulating auditory prostheses such as cochlear implants and auditory brainstem stimulators. It is to be appreciated that monitoring techniques presented herein may be used in connection with any of the above or other implantable auditory prostheses. However, merely for ease of description, embodiments of the present invention are primarily described herein with reference to a cochlear implant.

Figure 1:
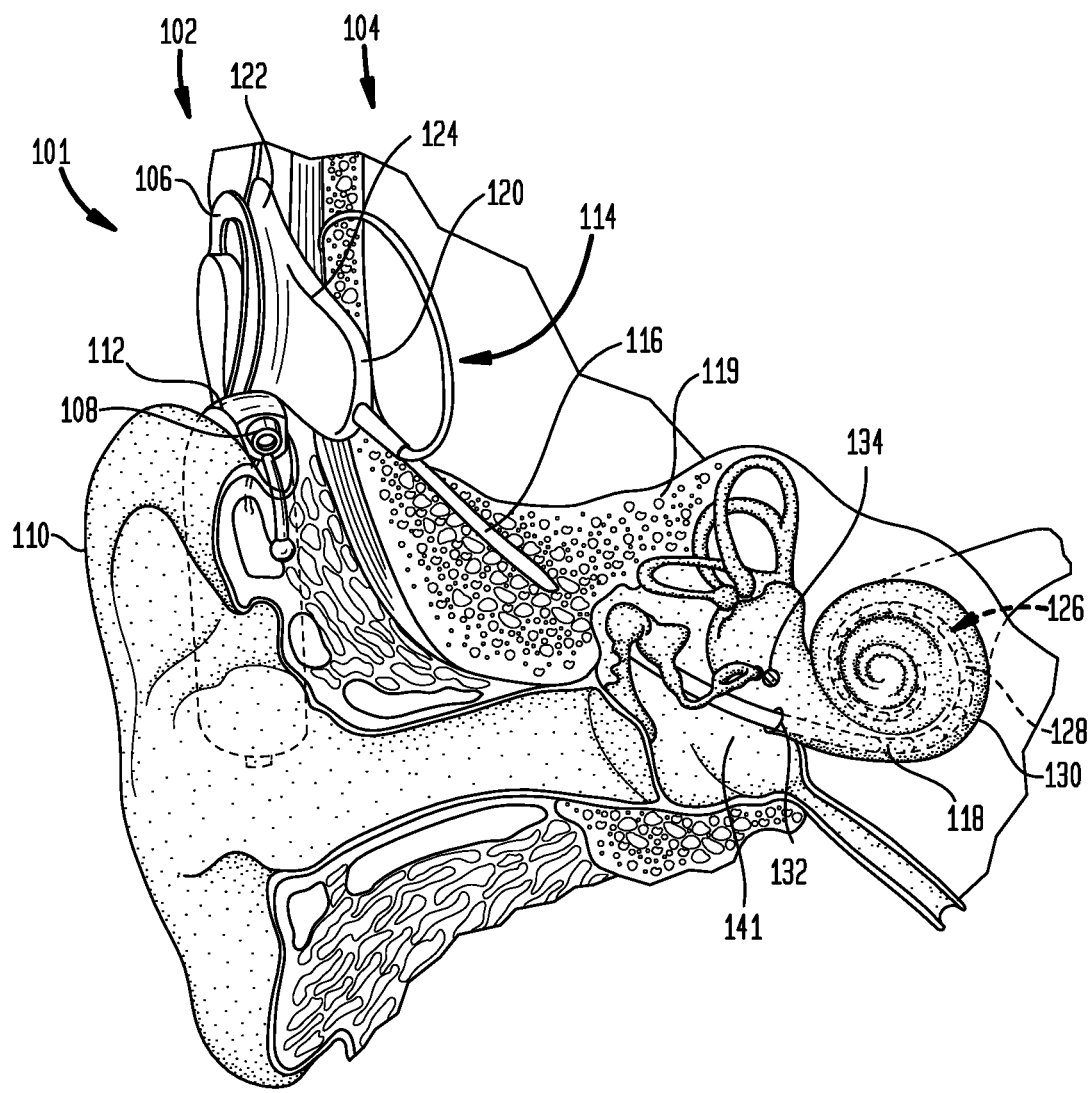
FIG. 1 is a schematic diagram of a cochlear implant in accordance with embodiments presented herein.

FIG. 1 is perspective view of an exemplary cochlear implant 100 in accordance with embodiments presented herein. The cochlear implant 100 includes an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more sound input elements 108 (e.g., microphones, telecoils, etc.) for detecting sound and a sound processing unit 112. The sound processing unit 112 may include, for example, a power source (not shown in FIG. 1) and a sound processor (also not shown in FIG. 1). The sound processor is configured to process electrical signals generated by a sound input element 108 that is positioned, in the depicted embodiment, by auricle 110 of the recipient. The sound processor provides the processed signals to external coil 106 via a cable (not shown in FIG. 1).

The implantable component 104 comprises an implant body 114, a lead region 116, and an elongate intra-cochlear stimulating assembly 118. The implant body 114 comprises a stimulator unit 120, an internal/implantable coil 122, and an internal receiver/transceiver unit 124, sometimes referred to herein as transceiver unit 124. The transceiver unit 124 is connected to the internal coil 122 and, generally, a magnet (not shown) fixed relative to the internal coil 122.

The magnets in the external component 102 and implantable component 104 facilitate the operational alignment of the external coil 106 with the internal coil 122. The operational alignment of the coils enables the implantable coil 122 to transmit/receive power and data to/from the external coil 106. More specifically, in certain examples, external coil 106 transmits electrical signals (e.g., power and stimulation data) to implantable coil 122 via a radio frequency (RF) link. Implantable coil 122 is typically a wire antenna coil comprised of multiple turns of electrically insulated single-strand or multi-strand platinum or gold wire. The electrical insulation of implantable coil 122 is provided by a flexible molding (e.g., silicone molding). In use, transceiver unit 124 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 is configured to be at least partially implanted in cochlea 130 and includes a plurality of intra-cochlear contacts 128. The contacts 128 collectively form a contact array 126 and may comprise electrical contacts and/or optical contacts.

Stimulating assembly 118 extends through an opening in the cochlea 130 (e.g., cochleostomy 132, the round window 134, etc.) and has a proximal end connected to stimulator unit 120 via lead region 116 that extends through mastoid bone 119. Lead region 116 couples the stimulating assembly 118 to implant body 114 and, more particularly, stimulator unit 120.

An intra-cochlear stimulating assembly, such as stimulating assembly 118, may be a perimodiolar stimulating assembly or a non-perimodiolar stimulating assembly. A perimodiolar stimulating assembly is a stimulating assembly that is configured to adopt a curved configuration during and/or after implantation into the recipient's cochlea so as to have a distal section positioned close to the wall of the recipient's modiolus (i.e., close to the modiolar wall). The modiolus is a conical shaped central region in the cochlea around which the cochlea canals (i.e., scala tympani, scala media, and scala vestibule) spiral. The modiolus consists of spongy bone in which the cochlea nerve cells, sometimes referred to herein as the spiral ganglion cells, are situated. The cochlea canals generally turn 2.5 times around the modiolus.

In general, the sound processor in sound processing unit 112 is configured to execute sound processing and coding to convert a detected sound into a coded signal corresponding to electrical signals for delivery to the recipient. The coded signal generated by the sound processor is then sent to the stimulator unit 120 via the RF link between the external coil 106 and the internal coil 122. The stimulator unit 120 includes one or more circuits that use the coded signals, received via the transceiver unit 124, so as to output a series of electrical stimulation signals (stimulation current) via one or more stimulation channels that terminate in the intra-cochlear stimulating contacts 128. As such, the stimulation current is delivered to the recipient via the intra-cochlear stimulating contacts 128. In this way, cochlear implant 100 stimulates the recipient's auditory nerve cells, bypassing absent or defective hair cells that normally transduce acoustic vibrations into neural activity.

To insert an intra-cochlear stimulating assembly 118 into a recipient, an opening (facial recess) is created through the recipient's mastoid bone 119 to access the recipient's middle ear cavity 141. The surgeon creates an opening from the middle ear into the cochlea 130 through, for example, the round window, oval window, the promontory, etc. of the cochlea 130. The surgeon then gently pushes the stimulating assembly 118 forward into the cochlea 130 until the stimulating assembly 118 achieves a desired position.

In conventional intra-cochlear stimulating assembly insertion techniques, the surgeon operates "blind." That is, due to the nature of the access (through the facial recess and the middle ear cavity), the surgeon cannot actually see the stimulating assembly 118 once it passes into the cochlea 130. Therefore, the surgeon relies upon only touch/feel during the insertion.

Most stimulating assembly insertions occur without incident, which is attributed to the design of the stimulating assembly, surgical guidelines, and surgeon skill. However, there are occasions when events occur during stimulating assembly insertion which can be called "adverse" in that the event may cause increased trauma to the cochlea, and/or negatively impact the performance or placement of the stimulating assembly.

Figure 2A:
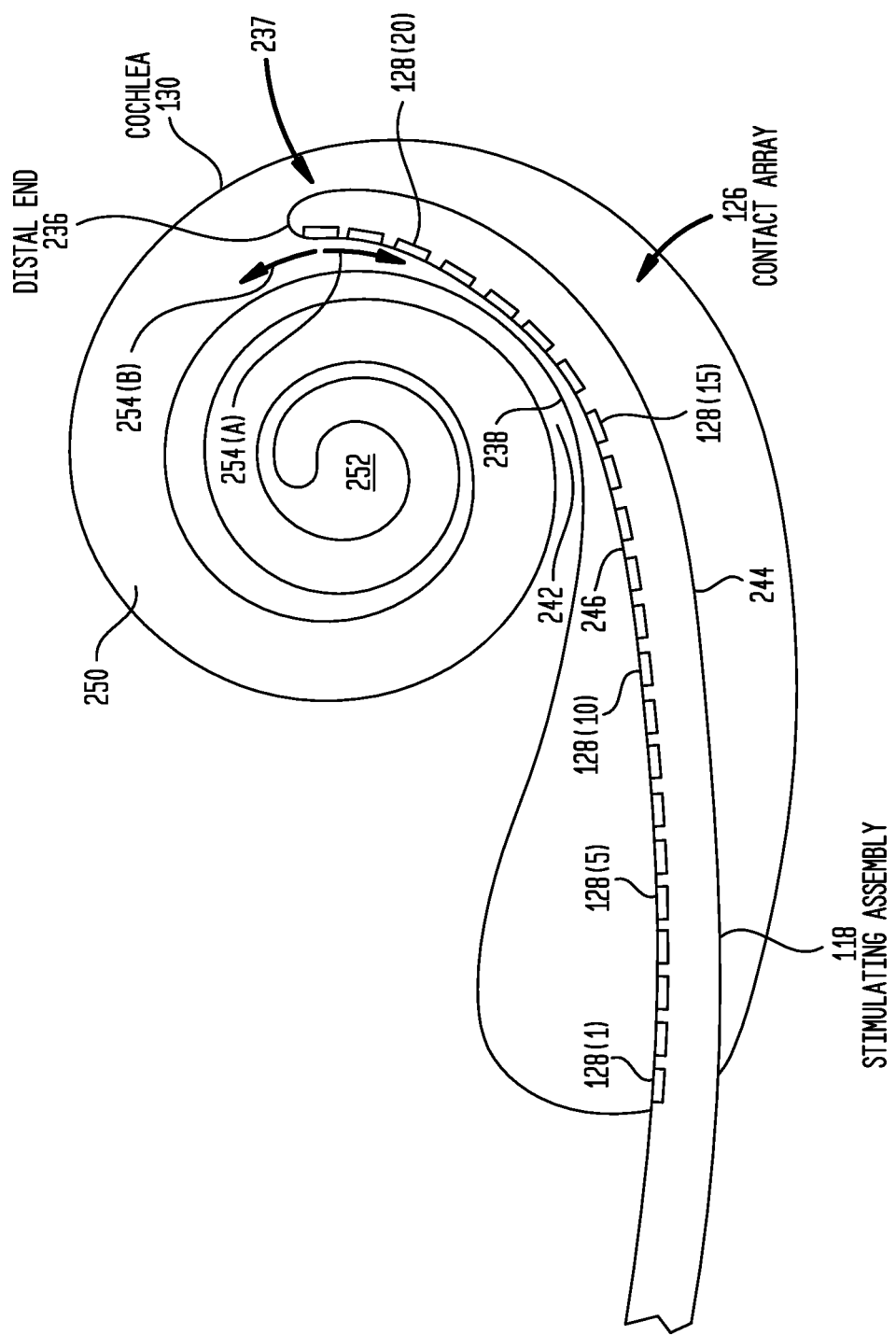
FIG. 2A is schematic diagram of a stimulating assembly during normal insertion into a recipient's cochlea.
Figure 2B:
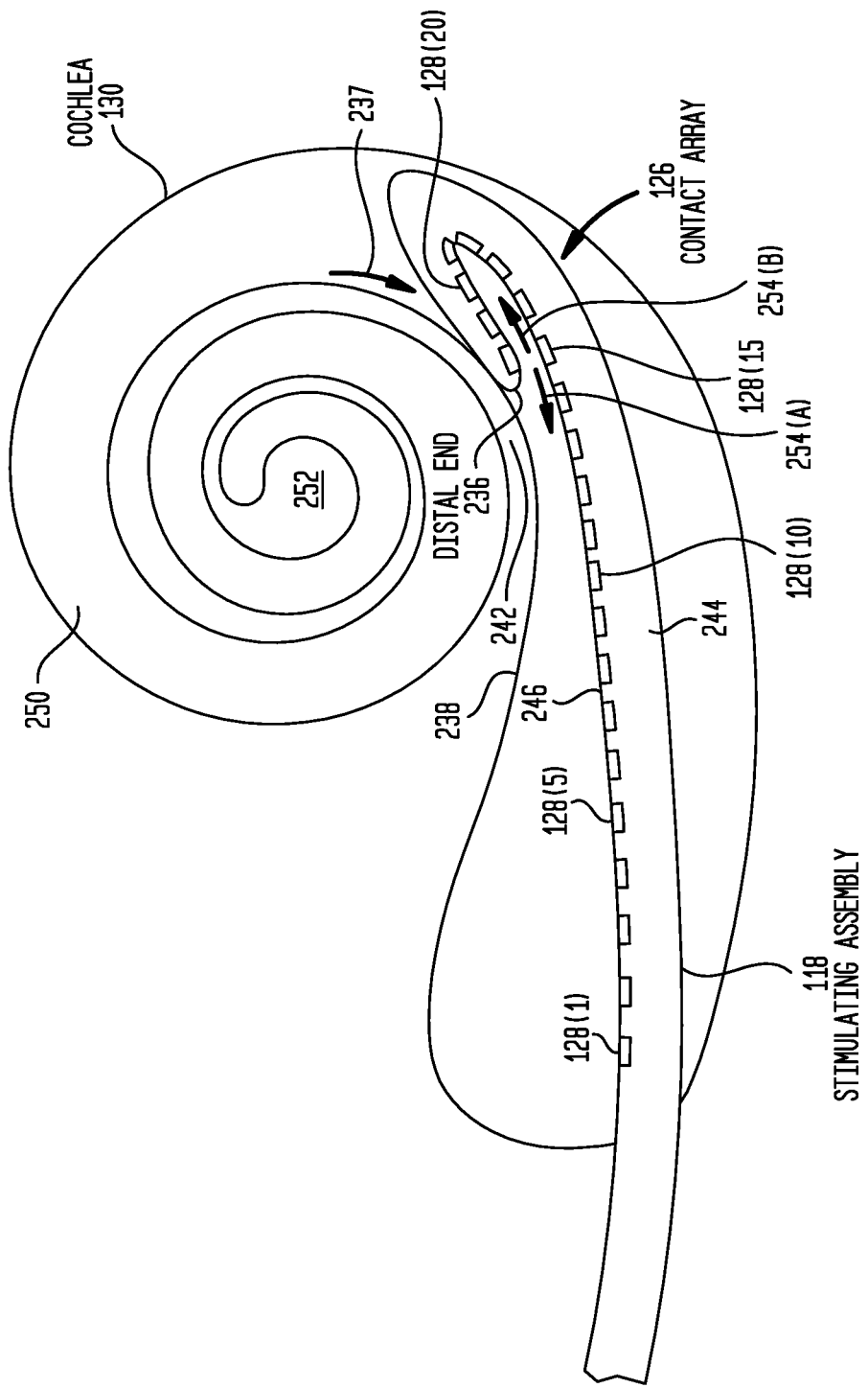
FIG. 2B is a schematic diagram illustrating an adverse event that may occur during insertion of a stimulating assembly into a recipient's cochlea.
Figure 2C:
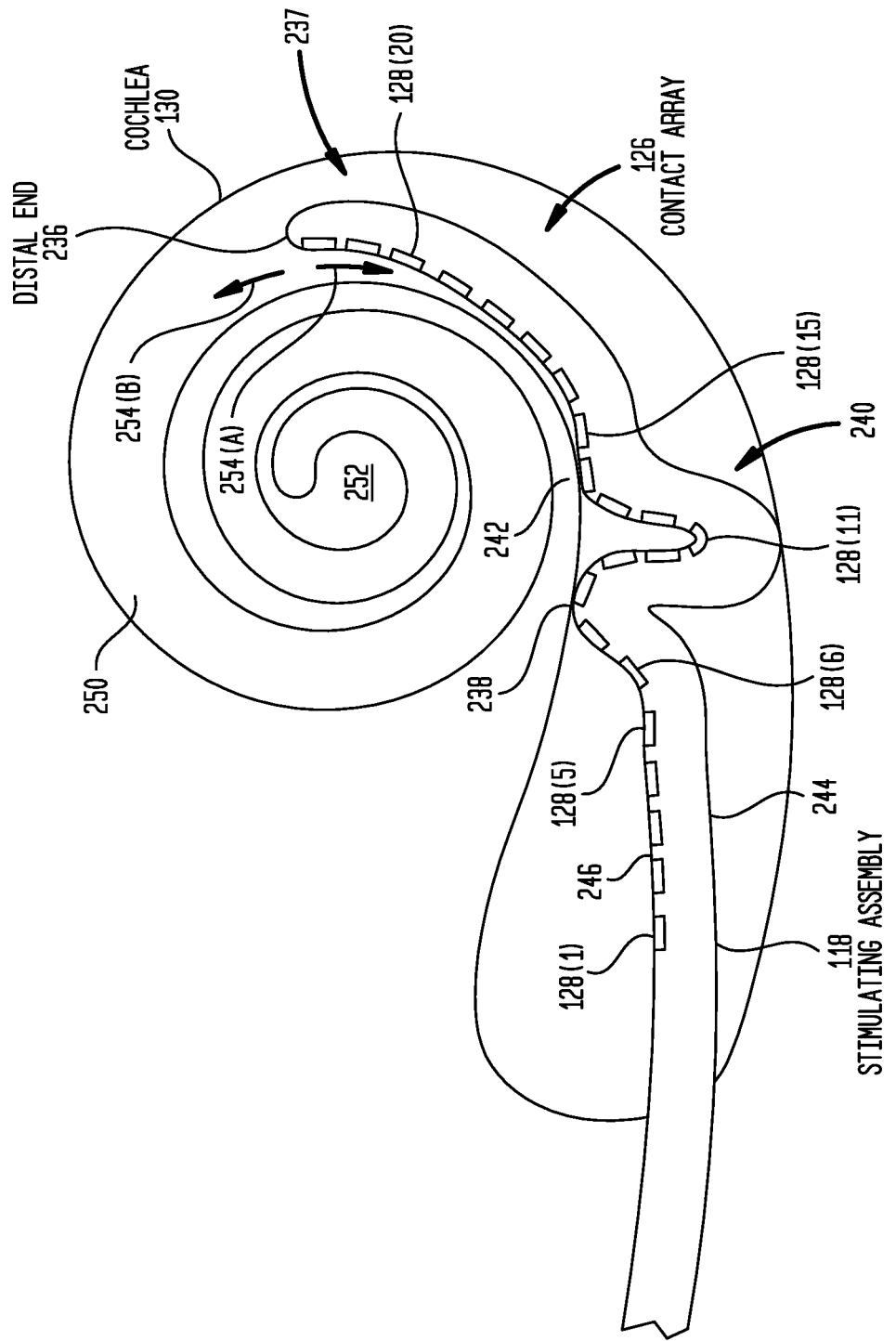
FIG. 2C is a schematic diagram illustrating another adverse event that may occur during insertion of a stimulating assembly into a recipient's cochlea.

FIG. 2A illustrates stimulating assembly 118 during a normal (good) insertion into a recipient's cochlea 130 (i.e., an insertion where no adverse events occur). FIGS. 2B and 2C illustrate several adverse events that may occur during insertion of the stimulating assembly 118 into the recipient's cochlea 130.

The stimulating assembly 118 comprises a carrier member 244 formed from a resiliently flexible material, such as silicone. A plurality of spaced contacts 128 are mounted or disposed in/on at least a first surface 246 of the carrier member 244 and collectively form a contact array 126. It should be appreciated that as used herein, particular combinations of the terms mounted/disposed, in/on, etc., are not to be interpreted to refer to any particular manufacturing technique or structural relationship.

In the specific examples of FIGS. 2A-2C, the stimulating assembly 118 includes twenty-two (22) intra-cochlear contacts. For ease of reference, the contacts 128 are numbered sequentially as contacts 128(1)-128(22) such that contact 128(1) is the most proximal contact (i.e., the contact disposed at the proximal end of the contact array 126) and contact 128(22) is the most distal contact (i.e., the contact disposed at the distal end/tip 236 of the contact array 126). It is to be appreciated that the number of contacts shown in FIGS. 2A-2C is merely illustrative and different numbers of contacts may be present in other embodiments.

As noted above, FIG. 2A illustrates a normal insertion where the stimulating assembly 118 travels smoothly through the cochlea canal (e.g., the scala tympani) 250. That is, as the surgeon inserts the stimulating assembly 118, the distal end 236 (i.e., the most apical end of distal region 237) travels towards the cochlea apex 252 without the occurrence of any adverse events. In contrast, FIG. 2B illustrates an example where obstacles, friction and/or other forces cause the distal end 236 of the stimulating assembly 118 to stick to (i.e., get caught on) a wall, such as inner wall 238, of the cochlea 130 instead of travelling smoothly down the length of the cochlea. In this example, not only can the surgeon not see that the distal end 236 is caught on the inner wall 238, but he/she also may not feel the resistance provided by the wall. As such, the surgeon may continue to push the stimulating assembly 118 into the cochlea 130 and the stimulating assembly may fold over onto itself. This type of event is generally referred to as tip foldover and could cause damage to the soft tissue structures within the cochlea, resulting in trauma and potential loss of residual hearing. Additionally, the contacts of stimulating assembly 118 within the "folded" region (e.g., 128(22)-128(18) in FIG. 2B) may become unusable, reducing the benefit of the cochlear implant 100 for the recipient.

In a further example shown in FIG. 2C, the stimulating assembly 118 deforms or buckles at a point along the length of the stimulating assembly, shown as region 240. Deformation may occur, for example, when the distal end 236 of the stimulating assembly 118 catches onto a structure inside the cochlea 130 within its insertion path. Deformation, which cannot be seen by the surgeon, may result in damage to the soft tissue structures. Additionally, the contacts of stimulating assembly 118 within the "deformed" region (e.g., contacts 128(14)-128(8) in FIG. 2C) may also become unusable, resulting in a reduction in hearing performance for the recipient. Deformation may also prevent the stimulating assembly 118 from assuming an optimal placement, such as a position close to the modiolus 242.

As noted above, these adverse events may detract from the benefit of the cochlear implant to the recipient, namely by increasing trauma and decreasing performance. Most surgeons use post-operative X-rays to check for the occurrence of these adverse events. Since these X-rays are taken after the wound is closed, the correction of adverse events requires the surgeon to re-open the wound. Presently, there are no techniques that provide a surgeon with real-time information about the physical state of the stimulating assembly in the cochlea. Instead, as noted, evidence of an adverse event only becomes available to the surgeon if post-operative checks are performed.

Presented herein are techniques for real-time (e.g., intra-operative) monitoring of the physical state of an implantable stimulating assembly in order to provide real-time feedback on the occurrence of adverse events within the cochlea, thereby assisting surgeons in obtaining immediate information about the quality of the stimulating assembly insertion. The physical state of the stimulating assembly refers to the shape/configuration of the stimulating assembly within the recipient's cochlea, brainstem, etc. In general, the physical state monitoring techniques presented herein use variations in measured electrical parameters (electrical data), such as voltages and impedances, taken from various locations along a contact array to provide an indication of the physical state of the stimulating assembly and, as such, whether any adverse events have occurred during insertion.

Evidence of adverse events such as tip foldover and deformation/buckling can be derived from information about the location of stimulating assembly contacts relative to one another within the space of the cochlea. That is, the incorrect positioning and/or obstruction of the stimulating assembly caused by an adverse event may bring certain stimulating assembly contacts closer to one another than would normally occur in a normal (good) insertion. The unexpected close proximity of certain contacts results in changes in the direction of the electric field, leading to electrical measurements recorded at the stimulating assembly contacts that are distinct from those of a normal insertion. Such differences in electrical field direction are exploited by the proposed method for the purpose of detecting the occurrence of adverse events.

The electrical information can be obtained by delivering stimulation (i.e., current signals) from at least one point along the contact array and then recording electrical parameters (e.g., voltage or impedance) from at least one other point along the same contact array. These measurements can be performed in real-time, such that electrical data is obtained continuously throughout the insertion. Simple post-processing of the recorded data is only required for generating a plot of the electrical measurements.

The proposed techniques do not rely on the specific values of the measured data to determine whether an adverse event has occurred. Instead, the relative magnitudes of the recorded values and the shapes of the plots they generate are used for the determination. The data is analyzed for key characteristics and trends which indicate whether the insertion outcome is normal/expected or if any adverse events have occurred The techniques presented herein include several methods for monitoring the physical state of a stimulating assembly in order to, for example, detect the occurrence of adverse events during insertion of a stimulating assembly. The monitoring methods presented herein can demonstrate the physical state of the stimulating assembly using one single set of data points, namely one set of measurement data recorded for a selected number of contacts within the contact array in response to a single stimulation pattern. As described further below, the single stimulation pattern may refer to the delivery of localized current signals (with a subsequent measurement at each of a selected number of contacts) or the sequential delivery of bipolar current signals between a first contact and each of the selected number of contacts (with a subsequent measurement at each of the selected number of contacts). As described further below, the monitoring methods described herein may utilize various interfaces for initiating and controlling the electrical measurements using a cochlear implant, auditory brainstem implant, etc.

FIG. 3 is a flowchart of a first method 300 for monitoring the physical state of the stimulating assembly through the use of localized stimulation. The method 300 of FIG. 3 is sometimes referred to herein as a localized monitoring method as the method uses the delivery of localized stimulation (i.e., current signals) to induce voltages at a plurality of other contacts. For ease of illustration, method 300 will be described with reference to the cochlear implant 100 of FIG. 1 and details of stimulating assembly 118 shown in FIGS. 2A-2C.

Method 300 begins at 302 where stimulation (i.e., one or more current signals) is delivered/sourced at a selected intra-cochlear contact. In one specific example, the stimulation is delivered at the most distal/apical contact 128(22) and is sunk at the second most distal contact 128(21) (i.e., the contact adjacent to contact 128(22)). The contact that delivers the current signals, namely contact 128(22), is sometimes referred to herein as the "stimulating" or "source" contact and the contact that sinks the current signals, namely contact 128(21), is sometimes referred to herein as the "return" contact. Additionally, the two contacts between which the stimulation is delivered (i.e., the most distal/apical contacts in the embodiment of FIG. 3) are collectively referred to herein as a "stimulating pair." The remaining contacts that are not part of the stimulating pair are disconnected from the system ground (i.e., are electrically "floating").

In general, two intra-cochlear contacts are selected for delivery of the stimulation. However, alternative embodiments may use an extra-cochlear contact to source/sink current. Additionally, it is to be that the use of the most distal contacts for sourcing/sinking the current is illustrative and other contacts could be used in alternative embodiments.

As noted above, the stimulating assembly 118 is inserted into the recipient's scala tympani 250. The scala tympani 250 is substantially filled with a conductive fluid known as perilymph. As such, when current signals are delivered at one of the intra-cochlear contacts, at least a portion of the current will spread through the perilymph. For example, as shown in FIGS. 2A-2C, following delivery of current signals at contact 128(22), the conductive nature of the perilymph will cause at least some current to flow away from the contact in the general directions illustrated by arrows 254(A) and 254(B). The flow of the current through the perilymph will cause the generation of voltages at the other intra-cochlear stimulating contacts. That is, although the stimulus is localized, due to the conductive perilymph the electric field spreads and induces voltage at the other contacts.

At 304, following the delivery of the current signals at contact 128(22), voltage measurements are performed at a selected number of other intra-cochlear contacts. That is, the voltage induced at the selected other contacts as a result of the delivery of the current signals at contact 128(22) is measured. The contacts at which the voltages are measured are sometimes referred to herein as "measurement" contacts. In the embodiment of FIG. 3, the measurement contacts may include any of the contacts 128(1)-128(22).

In certain circumstances, the cochlear implant 100 associated with stimulating assembly 118 is configured to make a plurality of voltage measurements at substantially the same time in response to the delivery of stimulation. In such embodiments, a single set of localized current signals is applied and the voltage induced at a selected number of the measurement contacts is measured substantially simultaneously at the measurement contacts. In other embodiments, the cochlear implant 100 is configured to measure the voltage at a single contact in response to the delivery of a set of current signals. In such embodiments, a plurality of sets of localized current signals are applied in sequence at contact 128(22), and a voltage is measured at a different contact after each sequential stimulation. As such, in the context of FIG. 3, the delivery of single stimulation pattern may refer to the delivery of one set of current signals (with subsequent substantially simultaneous measurement at each of the selected measurement contacts) or the sequential delivery of plurality of sets of current signals (with subsequent measurement at one of the selected measurement contacts after each set of current signals are delivered).

As noted above, stimulation delivered at a contact will have an effect on the other contacts, and the effect may depend on a number of factors. However, a primary factor that controls the effects of stimulation is the distance between the stimulating contact and the measurement contact. For example, in the embodiment of FIG. 3, when stimulation is delivered at contact 128(22), the voltage measured at other contacts should be increasingly smaller for contacts positioned farther from the stimulating contact 128(22). Therefore, at 306 of FIG. 3 the induced voltages measured at each of the measurement contacts in response to the single stimulation pattern are evaluated relative to one another to determine the relative distance between the stimulating contact 228(22) and each of the measurement contacts (i.e., the contacts at which voltages are measured). As described further below with reference to FIGS. 4A-4C, evaluation of the voltages relative to one another enables the determination of the physical state of the stimulating assembly 118. Also as described further below, based on the evaluation of measurements relative to one another, the cochlear implant 100 or a connected device may generate feedback to a surgeon or other user that provides information about the physical state of the stimulating assembly 118 and/or the occurrence of an adverse event.

Figure 4A:
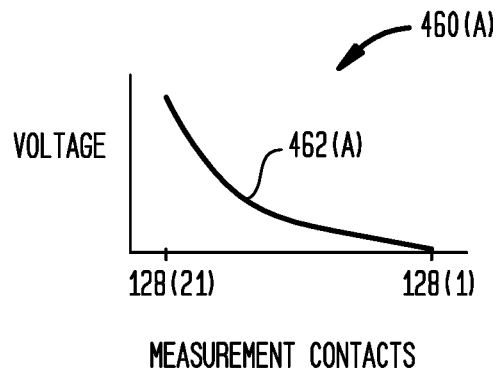
FIG. 4A is a graph illustrating electrical measurements obtained through the localized monitoring method of FIG. 3 during a normal insertion.

FIG. 4A is a graph 460(A) that illustrates the voltages measured during execution of the localized monitoring method 300 during a typical normal insertion (i.e., where no adverse events occur) in accordance with one embodiment. The graph 460(A) has a vertical (Y) axis that represents the measured voltage and a horizontal (X) axis that represents the selected measurement contacts 128(1)-128(21). The selected measurement contacts 128(1)-128(21) are shown on the horizontal axis in decreasing order (i.e., starting with measurement contact 128(21) closest to the stimulating contact 128(22)).

As noted, the stimulation is delivered at contact 128(22) and, as such, the measured voltage is highest at the measurement contact 128(21) that is positioned closest to stimulating contact 128(22). As shown in FIG. 4A, the voltage measured at each subsequent measurement contact decreases with increasing distance from the stimulating contact 128(22). That is, the measured voltages graphically appear as a decay curve 462(A), with the maximum recorded voltage occurring at the measurement contact 128(21) adjacent to the stimulating contact 128(22), and the minimum recorded voltage occurring at the most proximal measurement contact 128(1).

Figure 4B:
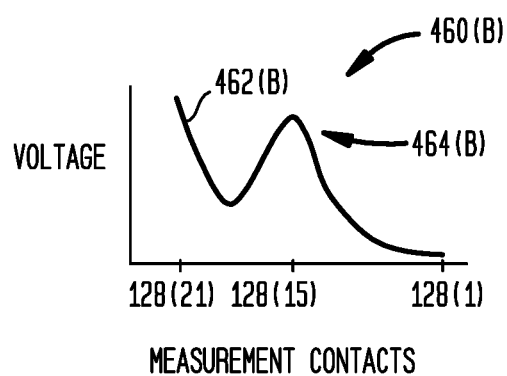
FIG. 4B is a graph illustrating electrical measurements obtained through the localized monitoring method of FIG. 3 during an insertion in which tip foldover occurs.

In contrast to FIG. 4A, FIG. 4B is a graph 460(B) that illustrates the voltages measured during execution of the localized monitoring method 300 during an insertion where an adverse event in the form of tip foldover, as shown in FIG. 2B, occurs. Similar to FIG. 4A, the graph 460(B) has a vertical axis that represents the measured voltage and a horizontal axis that represents the selected measurement contacts 128(1)-128(21). The selected measurement contacts 128(1)-128(21) are again shown on the horizontal axis in decreasing order.

As noted, the stimulus is delivered at contact 128(22) and, as such, the measured voltage is highest at the measurement contact 128(21) that is positioned closest to stimulating contact 128(22). As shown in FIG. 4B, the voltage measured at each subsequent measurement contact generally decreases with increasing distance from the stimulating contact 128 (22). That is, the measured voltages graphically appear as a decay curve 462(B), with the maximum recorded voltage occurring at the measurement contact 128(21) adjacent to the stimulating contact 128(22), and the minimum recorded voltage occurring at the most proximal measurement contact 128(1).

However, unlike the example of FIG. 4A, the decay curve 462(B) includes an abnormal/irregular region 464(B) that does not comply with the generally decreasing trend of FIG. 4A. The irregular region 464(B) of FIG. 4B is a voltage peak that indicates an increase in the voltage measured at contact 128(15). More specifically, the measured voltage generally decreases from measurement contact 128(20) through measurement contact 128(18). The measured voltage increases from measurement contact 128(18) through 128(15), then decreases from measurement contact 128(15) through 128 (1). The voltage increase from measurement contact 128(18) through 128(15), and the voltage peak at measurement contact 128(15), indicates that measurement contact 128(15) is located physically closer to the stimulating contact 128 (22) than at least measurement contacts 128(18) through 128(16) (and possibly other stimulating contacts). As noted above, this physical proximity between measurement contact 128(15) and the stimulating contact 128(22) is improper, indicating the occurrence of an adverse event. The specific shape of the irregular region 464(B) (i.e., a voltage peak with generally decreasing voltage on either side of the peak) indicates tip foldover.

Figure 4C:
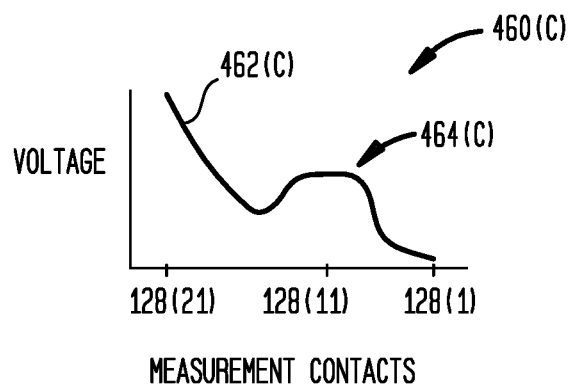
FIG. 4C is a graph illustrating electrical measurements obtained through the localized monitoring method of FIG. 3 during an insertion in which deformation occurs.

FIG. 4C is a graph 460(C) that illustrates the voltages measured during execution of the localized monitoring method 300 during an insertion where another adverse event in the form of deformation, as shown in FIG. 2C, occurs. Similar to FIG. 4A, the graph 460(C) has a vertical axis that represents the measured voltage and a horizontal axis that represents the selected measurement contacts 128(1)-128 (21). The selected measurement contacts 128(1)-128(21) are again shown on the horizontal axis in decreasing order.

As noted, stimulation is delivered at contact 128(22) and, as such, the measured voltage is highest at the measurement contact 128(21) that is positioned closest to stimulating contact 128(22). As shown in FIG. 4C, the voltage measured at each subsequent measurement contact generally decreases with increasing distance from the stimulating contact. That is, the measured voltages graphically appear as a decay curve 462(C), with the maximum recorded voltage occurring at the measurement contact 128(21) adjacent to the stimulating contact 128(21), and the minimum recorded voltage occurring at the most proximal measurement contact 128(1).

However, unlike the example of FIG. 4A, the decay curve 462(C) includes an abnormal/irregular region 464(C) that does not comply with the generally decreasing trend of FIG. 4A. The irregular region 464(C) of FIG. 4C is a generally flattened/tiered region indicating that the voltage measured at a plurality of measurement contacts is substantially the same. More specifically, the measured voltage generally decreases from measurement contact 128(20) through measurement contact 128(14). However, the voltage measured at measurement contacts 128(13) through 128(8) is substantially the same with only a minor drop at measurement contact 128(11). The measured voltage then decreases from measurement contact 128(7) through 128(1). The generally flattened/tiered region 464(C) indicates that measurement contacts 128(13) through 128(8) are all generally located substantially the same physical distance from the stimulating contact 128(22). This substantially same physical distance between measurement contacts 128(13) through 128(8) and the stimulating contact 128(22) is improper, indicating the occurrence of an adverse event. The specific shape of the irregular region 464(C) (i.e., a generally flattened region) indicates deformation at the region of measurement contacts 128(13) through 128(8).

The embodiments of FIGS. 3 and 4A-4C have been described with reference to the use of the two most distal contacts for delivering the localized stimulation. It is to be appreciated that the use of the two most distal contacts is illustrative and that other contacts may be used to deliver localized stimulation. For example, in one alternative embodiment, other contacts within distal region 237, such as contacts 128(21) or 120(20) could be used as the stimulating contact or the return contact. In another alternative arrangement, contacts 128(15) and 128(16), located within the mid-region of the stimulating assembly 118 may be used to deliver localized stimulation. Such embodiments may be used alone (e.g., if the distal contact and/or associated wire is broken), or in combination with the illustrative embodiment of FIG. 3 (e.g., as a confirmation mechanism).

The embodiments of FIGS. 3 and 4A-4C have also been described with reference to measurement of voltage values at the measurement contacts. Other embodiments may deliver localized stimulation in the same manner as described above, but then measure the impedance at the measurement contacts. The impedance measurements could then be used to determine the physical state of the stimulating assembly.

In summary, FIGS. 3 and 4A-4C illustrate localized monitoring techniques where stimulation occurs between two contacts and electrical parameters (e.g., voltage or impedance) are taken from consecutive contacts along the stimulating assembly. The electrical measurements are evaluated relative to one another to determine relative distances and thus determine the physical state/location of the stimulating assembly, thereby enabling the detection of adverse events.

FIG. 5 is a flowchart of another method 500 for monitoring the physical state of the stimulating assembly through the use of bipolar stimulation. As such, the method 500 of FIG. 5 is sometimes referred to herein as a bipolar monitoring method. For ease of illustration, method 500 will be described with reference to the cochlear implant 100 of FIG. 1 and details of stimulating assembly 118 shown in FIGS. 2A-2C.

Method 500 begins at 502 where stimulation (i.e., one or more current signals) is delivered between a first intra-cochlear contact and a second intra-cochlear contact. In one specific example, the stimulation is first delivered between the most distal/apical contact 128(22) and at the second most distal contact 128(21) (i.e., the contact adjacent to contact 128(22)). The contact that delivers the current signals, namely contact 128(22), is sometimes referred to herein as the "stimulating" or "source" contact and the contact that sinks the current, namely contact 128(21), is sometimes referred to herein as the "return" contact. Additionally, the two contacts between which the stimulation is delivered (e.g., the two most distal/apical contacts) are collectively referred to herein as a "stimulating pair." The remaining contacts that are not part of the stimulating pair are disconnected from the system ground (i.e., are electrically "floating").

In general, two intra-cochlear contacts are selected for delivery of the bipolar stimulation. However, alternative embodiments may use an extra-cochlear contact to source/sink current.

At 504, following the delivery of the current signals between the stimulating contact 128(22) and the return contact 128(21), an electrical measurement is performed at the return contact. For example, the voltage induced at the return contact 128(21) as a result of the delivery of the current signals at contact 128(22) is measured. Since an electrical measurement is performed at the return contact 128(21), the return contact is sometimes referred to herein as a "measurement" contact.

The bipolar monitoring method 500 utilizes a plurality of electrical measurements made at a selected number of different contacts to determine a physical state of the stimulating assembly 118. As such, electrical measurements need to also be made at additional contacts (i.e., other than contact 128(21)). Accordingly, at 506, a determination is made as to whether electrical measurements have been made at all of a selected number of the contacts. Similar to the embodiment of FIG. 3, the contacts at which measurements may be performed are sometimes referred to herein as measurement contacts. Any of the contacts 128(1)-128(22) may operate as measurement contacts as they may be used to perform electrical measurements.

If it is determined at 506 that electrical measurements have not been made at all of the selected number of measurement contacts, then at 508 another measurement contact is made the return contact of the stimulating pair. For example, contact 128(20) (i.e., the next contact in the contact array 126) may be made the return contact by electrically connecting the contact 128(20) to ground and disconnecting the previous return contact (i.e., contact 128(21)) from ground (i.e., so that the previous return contact is electrically floating). As a result, the stimulating pair then comprises stimulating contact 128(22) and measurement contact 128(20).

After changing the return contact, method 500 returns to 502 where stimulation is delivered between stimulating contact 128(22) and the return contact 128(20). At 504, following the delivery of the current signals between the stimulating contact 128(22) and the return contact 128(20), an electrical measurement is performed at the return contact. Method 500 then returns to 506 for another determination of whether electrical measurements have been made at all of the selected number of measurement contacts. The loop defined by 508, 502, 504, and 506 continues until measurements are made at all of the selected measurement contacts.

Once it is determined at 506 that measurements have been made at all of the selected measurement contacts, method 500 proceeds to 510 where the electrical measurements are evaluated relative to one another to determine the relative proximity between the stimulating contact 228(22) and each of the measurement contacts. As described further below with reference to FIGS. 5A-5C, evaluation of the measurements relative to one another enables the determination of the physical state of the stimulating assembly 118. Also as described further below, based on the evaluation of measurements relative to one another, the cochlear implant 100 or a connected device may generate feedback to a surgeon or other user that provides information about the physical state of the stimulating assembly 118 and/or the occurrence of an adverse event.

Figure 6A:
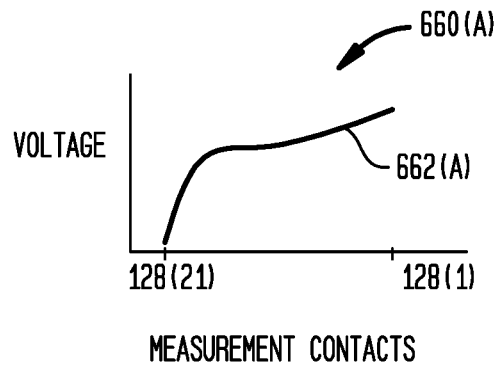
FIG. 6A is a graph illustrating electrical measurements obtained through the bipolar monitoring method of FIG. 5 during a normal insertion.

FIG. 6A is a graph 660(A) that illustrates the voltages measured during execution of the bipolar monitoring method 500 during a typical normal insertion (i.e., where no adverse events occur) in accordance with one embodiment. The graph 660(A) has a vertical axis that represents measured bipolar voltages and a horizontal axis that represents the selected measurement contacts 128(1)-128(21). The selected measurement contacts 128(1)-128(21) are shown on the horizontal axis in decreasing order (i.e., starting with measurement contact 128(21) closest to the stimulating contact 128(22)).

For a properly inserted stimulating assembly, the measured bipolar voltage increases towards the basal end of the stimulating assembly. That is, as the distance between the stimulating contact 128(22) and a measurement contact increases, the bipolar voltage also increases. Therefore, as shown in FIG. 6A, the measured bipolar voltages graphically appear as a growth curve 662(A), with the minimum voltage occurring at measurement contact 128(21) adjacent to the stimulating contact 128(22) and the maximum voltage occurring at the most proximal/basal measurement contact 128(1).

Figure 6B:
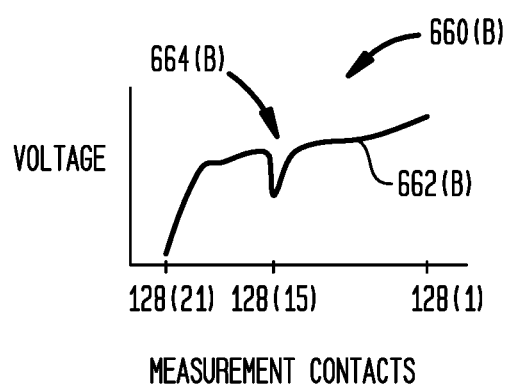
FIG. 6B is a graph illustrating electrical measurements obtained through the bipolar monitoring method of FIG. 5 during an insertion in which tip foldover occurs.

FIG. 6B is a graph 660(B) that illustrates the bipolar voltages measured during execution of the bipolar monitoring method 500 during an insertion where an adverse event in the form of tip foldover, as shown in FIG. 2B, occurs. Similar to FIG. 6A, the graph 660(B) has a vertical axis that represents the measured bipolar voltage and a horizontal axis that represents the selected measurement contacts 128(1)-128(21). The selected measurement contacts 128(1)-128(21) are again shown on the horizontal axis in decreasing order.

As shown in FIG. 6B, the measured bipolar voltage generally increases at each subsequent measurement contact with increasing distance from the stimulating contact 128(22). That is, growth curve 662(B) illustrates that as the distance between the stimulating contact 128(22) and a measurement contact increases, the bipolar voltage also generally increases. However, unlike the example of FIG. 6A, the growth curve 662(B) includes an abnormal/irregular region 664(B) that does not comply with the generally increasing trend of FIG. 6A. The irregular region 664(B) of FIG. 6B is a voltage trough that indicates a decrease in the voltage measured around contact 128(15). The voltage decrease around contact 128(15) indicates that measurement contact 128(15) is unexpectedly located physically closer to the stimulating contact 128(22). This physical proximity between measurement contact 128(15) and the stimulating contact 128(22) is improper, indicating the occurrence of an adverse event. The specific shape of the irregular region 664(B) (i.e., a voltage trough with voltage increases on either side of the trough) indicates tip foldover.

Figure 6C:
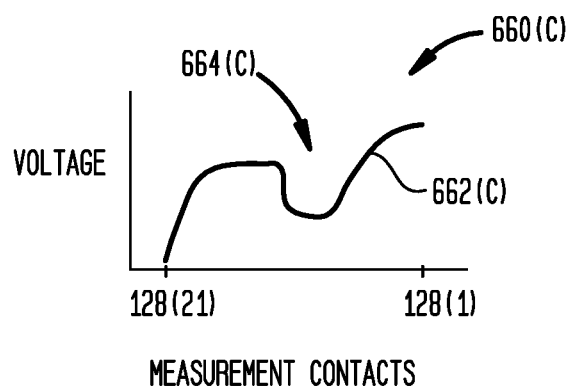
FIG. 6C is a graph illustrating electrical measurements obtained through the bipolar monitoring method of FIG. 5 during an insertion in which deformation occurs.

FIG. 6C is a graph 660(C) that illustrates the bipolar voltages measured during execution of the bipolar monitoring method 500 during an insertion where another adverse event in the form of deformation, as shown in FIG. 2C, occurs. Similar to FIG. 6A, the graph 660(C) has a vertical axis that represents the measured bipolar voltage and a horizontal axis that represents the selected measurement contacts 128(1)-128(21). The selected measurement contacts 128(1)-128(21) are again shown on the horizontal axis in decreasing order.

As shown in FIG. 6B, the measured bipolar voltage generally increases at each subsequent measurement contact with increasing distance from the stimulating contact 128 (22). That is, growth curve 662(B) illustrates that as the distance between the stimulating contact 128(22) and a measurement contact increases, the bipolar voltage also increases. However, unlike the example of FIG. 6A, the curve 662(C) includes an abnormal/irregular region 664(C) that does not comply with the generally increasing trend of FIG. 6A. The irregular region 664(C) of FIG. 6C is a generally flattened/tiered region indicating that the voltage measured at a plurality of measurement contacts is substantially the same. More specifically, the measured voltage generally increases from measurement contact 128(21) through measurement contact 128(14). However, the voltage measured at measurement contacts 128(13) through 128(8) is substantially the same with only a minor increase at measurement contact 128(11). The voltage then increases from measurement contact 128(7) through 128(1). The generally flattened/tiered region 664(C) indicates that measurement contacts 128(13) through 128(8) are all generally located substantially the same physical distance from the stimulating contact 128(22). This substantially same physical proximity between measurement contacts 128(13) through 128(8) and the stimulating contact 128(22) is improper, indicating the occurrence of an adverse event. The specific shape of the irregular region 664(C) (i.e., a generally flattened region) indicates deformation at the region of measurement contacts 128(13) through 128(8).

The embodiments of FIGS. 6 and 6A-6C have also been described with reference to measurement of voltage values at the measurement contacts. Other embodiments may deliver bipolar stimulation in the same manner as described above, but then measure the impedance at the measurement contacts. The impedance measurements could then be used to determine the physical state of the stimulating assembly.

In summary, FIGS. 5 and 6A-6C illustrate embodiments in which bipolar stimulation is delivered between one particular contact (i.e., the stimulating contact) and other contacts in the array in a sequential manner. Electrical parameters (e.g., voltage or impedance) taken from the return contacts are evaluated relative to one another to determine relative distances and thus determine the physical state/location of the stimulating assembly, thereby enabling the detection of adverse events.

The results of the evaluation conducted in the localized or bipolar monitoring methods can be presented as feedback to the surgeon or other user to provide an indication of the physical state of the stimulating assembly. The feedback may take a number of different forms in order to effectively portray the physical state information. For example, in one embodiment, a graph of the electrical measurements may be visually displayed to the surgeon. The surgeon, surgical assistant, etc. could monitor the graph for changes indicating an adverse event has occurred or is about to occur.

In another embodiment, other visual cues/feedback such as flashing lights, the display of an image of the estimated shape of the stimulating assembly, etc. may be used to indicate when an adverse event has occurred or is about to occur. For example, light emitting diodes (LEDs) on an external sound processor could be used to provide the visual cues to the surgeon.

In other embodiments, audible cues such as beeps or tones may be used to indicate when an adverse event has occurred or is about to occur. For example, an audible warning may be generated if it is determined that an event has occurred or is about to occur (e.g., an audible warning may be generated when the tip of the stimulating assembly becomes stuck or has begun to contact or perforate the basilar membrane). In a further embodiment, haptic (tactile) cues may be used to indicate when an adverse event has occurred or is about to occur. For example, vibrations or a buzzing may be generated if it is determined that an event has occurred or is about to occur. It is also to be appreciated that different types of feedback may be used in combination with one another (i.e., a visual presentation on a display screen along with an audible warning when an event has occurred or is about to occur).

Figure 7:
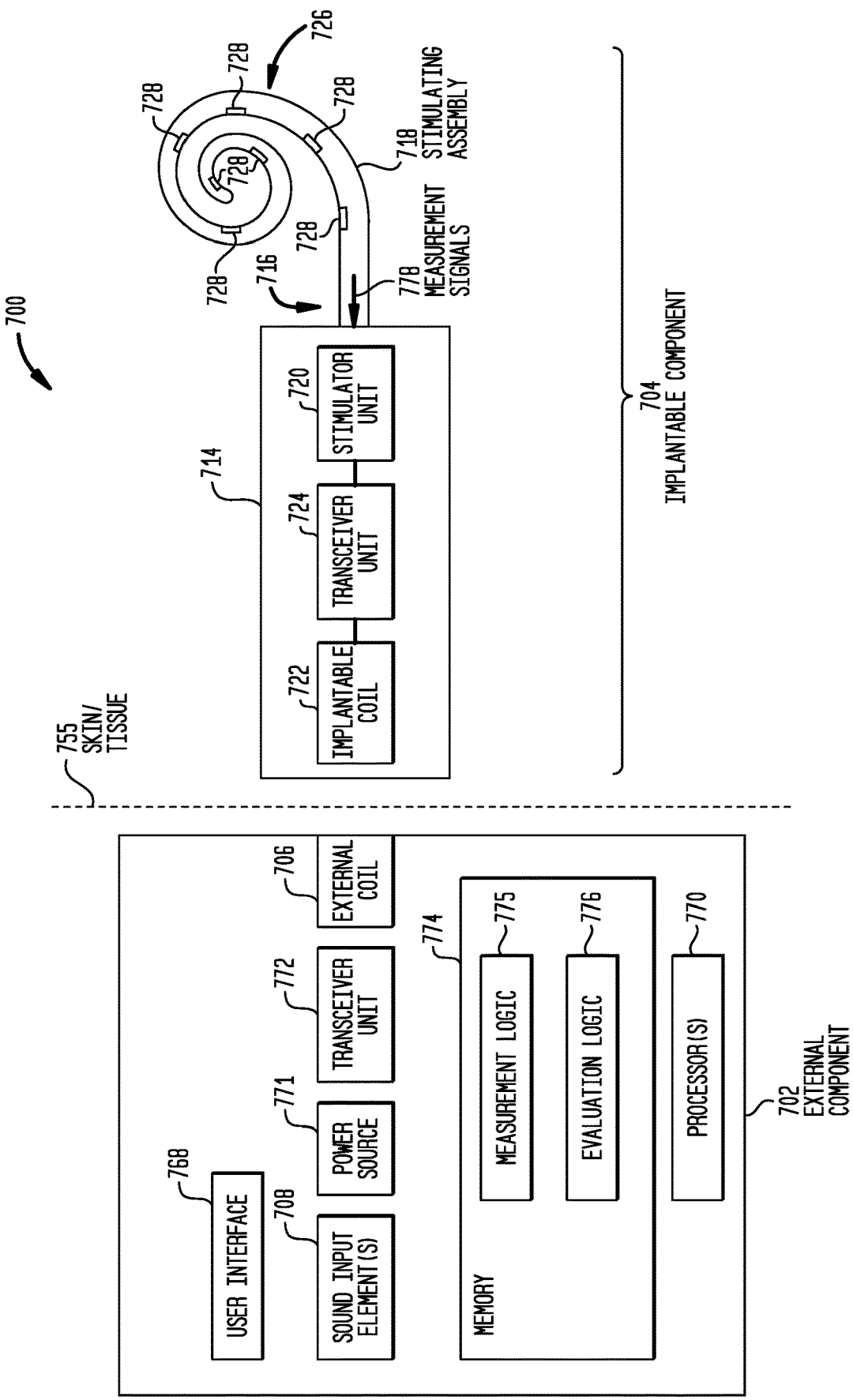
FIG. 7 is a block diagram of a cochlear implant configured to perform monitoring techniques in accordance with embodiments presented herein.

FIG. 7 is a block diagram illustrating further details of cochlear implant 700 configured for monitoring the physical state of a stimulating assembly in accordance with embodiments presented herein. The cochlear implant 700 comprises an external component 702 and an implantable component 704.

The implantable component 704 is disposed beneath a recipient's skin/tissue 755 and comprises an implant body 714 connected to the elongate stimulating assembly 718 via a lead region 716. The stimulating assembly 718 comprises a plurality of contacts 728 forming a contact array 726. For ease of illustration, only a subset of the contacts 728 in contact array 726 is shown in FIG. 7. The implant body 714 comprises a stimulator unit 720, a transceiver unit 724, and an implantable coil 722.

The external component 702 may be, for example, a behind-the-ear device, body-worn sound processor, coil (button) processor, etc. The external component 702 comprises a user interface 768, one or more sound input elements 708 (e.g., microphones, telecoils, etc.) for detecting sound, one or more processors 770 (e.g., including a sound processor), a power source 771 (e.g., battery), a transceiver unit 772, an external coil 706, and a memory 774. Memory 774 comprises measurement logic 775 and evaluation logic 776.

Memory 774 may comprise read only memory (ROM), random access memory (RAM), magnetic disk storage media devices, optical storage media devices, flash memory devices, electrical, optical, or other physical/tangible memory storage devices. One or more of the processors 770 are, for example, a microprocessor or microcontroller that executes instructions for the measurement logic 775 and evaluation logic 776. Thus, in general, the memory 774 may comprise one or more tangible (non-transitory) computer readable storage media (e.g., a memory device) encoded with software comprising computer executable instructions and when the software is executed (by a processor 770) it is operable to perform the operations described herein in connection with the monitoring methods described herein. More specifically, measurement logic 775 may be executed by the processor 770 to generate signals/commands that cause stimulator unit 720 to: (1) generate stimulation (i.e., localized stimulation or bipolar stimulation), and (2) obtain electrical measurements at the measurement contacts.

Evaluation logic 776 may be executed by a processor 770 to evaluate the measurements and generate feedback to a surgeon or other user. In the example of FIG. 7, the processor 770 that executes the measurement logic 775 and the evaluation logic 776 is sometimes referred to herein as an event detection processor.

Measurements are obtained by the stimulator unit 720 from measurement contacts 728(1)-728(21) as measurement signals 778. The measurement signals 778 may be transmitted to external component 702 for processing. That is, transceiver unit 724 transmits the measurement signals 778 to transceiver unit 772 via implantable coil 722 and external coil 706. Once the measurement signals 778 are received at the external component 702, the signals may be processed by processor 770 executing measurement logic 775. A processor 770 may further execute evaluation logic 776 to determine the physical state of stimulating assembly 718 and generate feedback to a user.

In certain embodiments, the measurement signals 778 may be stored in the memory 774 prior to use by the processor 770. The measurement signals 778 may be stored temporarily (e.g., during collection of measurements and/or for use during processing) or semi-permanently (i.e., for subsequent export to another device).

FIG. 7 illustrates an example in which cochlear implant 700 includes an external component 702 with an external sound processor. It is to be appreciated that the use of an external component is merely illustrative and that the monitoring techniques presented herein may be used in arrangements having an implanted sound processor (e.g., totally implantable cochlear implants). It is also to be appreciated that the individual components referenced herein, e.g., sound input elements 708 and the sound processor, may be distributed across more than one auditory prosthesis, e.g., two cochlear implants, and indeed across more than one type of device, e.g., cochlear implant 700 and a consumer electronic device or a remote control of the cochlear implant 700.

Figure 8:
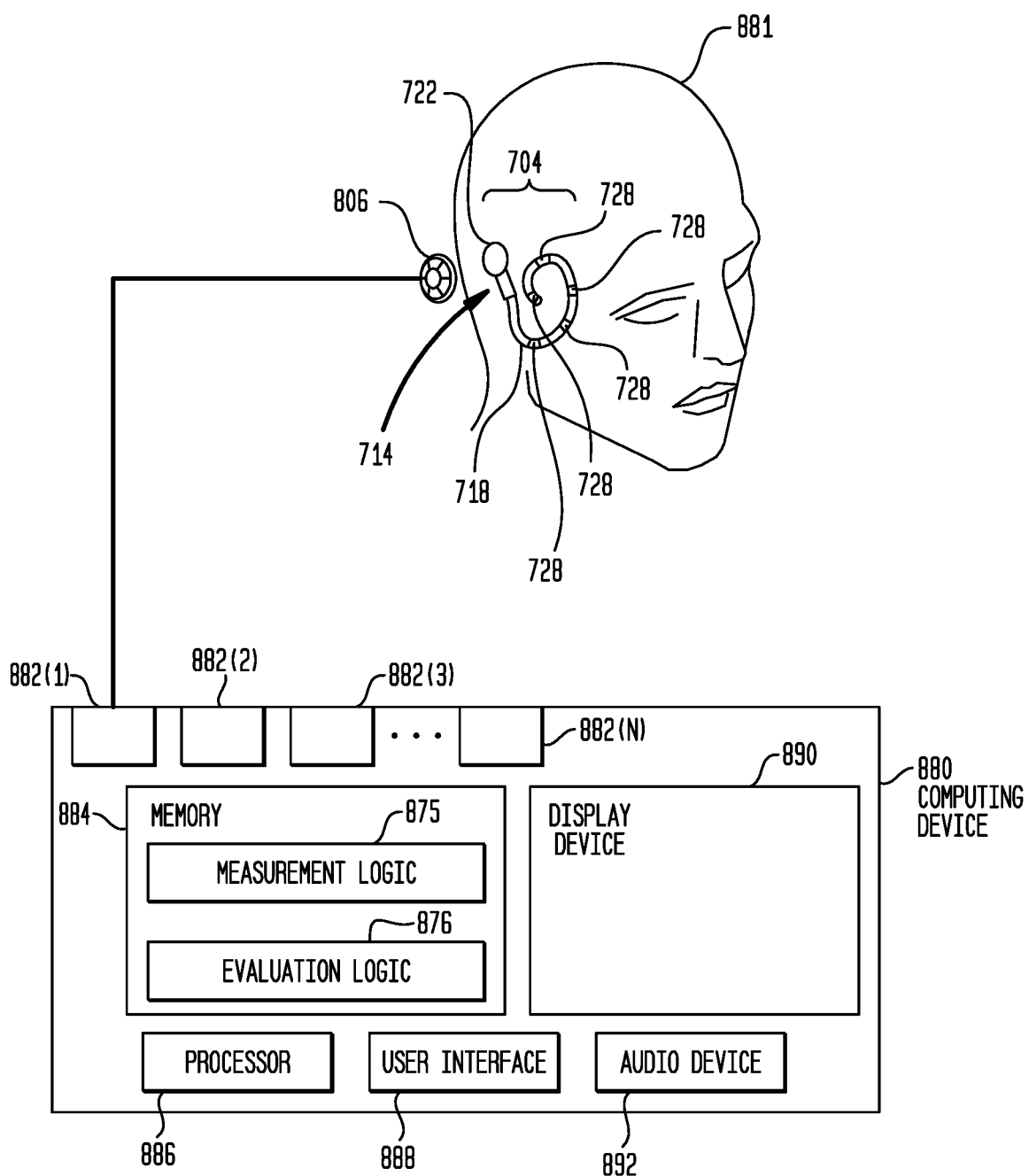
FIG. 8 is a block diagram of a processing configured to perform monitoring techniques in accordance with embodiments presented herein.

It is to be appreciated that the monitoring functionality may not necessarily form part of the cochlear implant as shown in FIG. 7. For example, FIG. 8 is a block diagram of an alternative arrangement in which the monitoring functionality is part of a separate computing device 880. For ease of reference, the embodiment of FIG. 8 will be described with reference to the implantation of implantable component 704 of FIG. 7 into a recipient 881.

The computing device 880 is a computing device that comprises a plurality of interfaces/ports 882(1)-882(N), a memory 884, a processor 886, a user interface 888, a display device (e.g., screen) 890, and an audio device (e.g., speaker) 892. The memory 884 comprises measurement logic 875 and evaluation logic 876.

The interfaces 882(1)-882(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 8, interface 882(1) is connected to an external coil 806 and/or an external device (not shown) in communication with the external coil. Interface 678(1) may be configured to communicate with the external coil 806 (or other device) via a wired or wireless connection (e.g., telemetry, Bluetooth, etc.).

Memory 884 may comprise ROM, RAM, magnetic disk storage media devices, optical storage media devices, flash memory devices, electrical, optical, or other physical/tangible memory storage devices. The processor 886 is, for example, a microprocessor or microcontroller that executes instructions for the measurement logic 875 and evaluation logic 876. Thus, in general, the memory 884 may comprise one or more tangible (non-transitory) computer readable storage media (e.g., a memory device) encoded with software comprising computer executable instructions and when the software is executed (by processor 886) it is operable to perform the operations described herein in connection with the monitoring methods described herein. More specifically, measurement logic 875 may be executed by the processor 886 to generate signals/commands that cause stimulator unit 720 to: (1) generate stimulation (i.e., localized stimulation or bipolar stimulation), and (2) obtain electrical measurements at the measurement contacts. Evaluation logic 876 may be executed by the processor 886 to evaluate the measurements and generate feedback to a surgeon or other user. In the example of FIG. 8, the processor 886 that executes the measurement logic 875 and the evaluation logic 876 is sometimes referred to herein as an event detection processor.

The computing device 880 may be any of a number of different hardware platforms configured to perform the monitoring techniques presented herein. In one embodiment, the computing device 880 is a computer (e.g., laptop computer, desktop computer, etc.) present within the operating theatre. In another embodiment, the computing device 880 is an intraoperative remote assistant. In a further embodiment, the computing device 880 is an off-the-shelf device, such as a mobile phone or tablet device, to which the measurement logic 875 and evaluation logic 876 is downloaded as an application or program. In these various embodiments of FIG. 8, both control of the measurements and the display/notification of evaluation results occur through the computing device 880.

Figure 9:
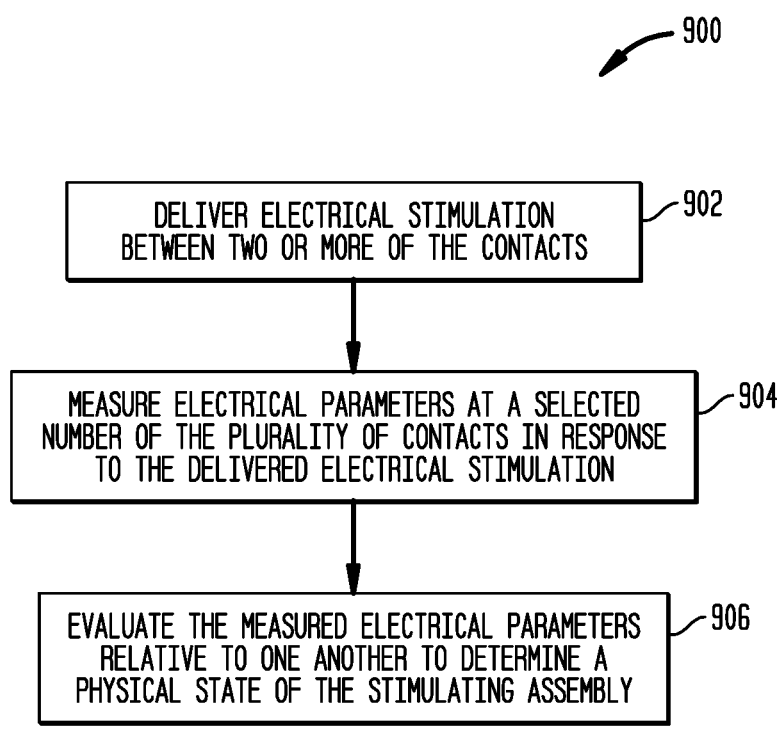
FIG. 9 is a flowchart of a method in accordance with embodiments presented herein.

FIG. 9 is a flowchart of a method 900 for monitoring a stimulating assembly comprising a plurality of longitudinally spaced contacts. Method 900 begins at 902 where electrical stimulation is delivered between two or more of the contacts. At 904, electrical parameters are measured at a selected number of the plurality of contacts in response to the delivered electrical stimulation. At 906, the measured electrical parameters are evaluated relative to one another to determine a physical state of the stimulating assembly As detailed above, presented herein are techniques for real-time (e.g., intraoperative) monitoring of a stimulating assembly to determine the physical state of the stimulating assembly and thus detect adverse events such as tip foldover or deformation. As described further below, the monitoring utilizes variations in electrical measurements such as impedance and voltage. A real-time algorithm utilizes the electrical measurements to determine the state of the stimulating assembly in the cochlea and thus detect tip foldover and/or deformation. In certain embodiments, the event detection techniques presented herein provide surgeons with a real-time indication that an adverse event has occurred, thereby enabling the surgeon to correct the insertion. This may provide improved confidence in the quality of the stimulating assembly insertion, reduce the need for revision surgery, and improve the hearing performance outcomes of recipients. The techniques presented herein may also enable consistent insertions across substantially all recipients, making the insertion process more repeatable regardless of the surgeon's experience. Confirming the state of the stimulating assembly during surgery also reduces the need for post-operative imaging, translating to cost and time benefits for recipients and hospitals, and reducing recipient exposure to radiation. Data obtained from each insertion may also be logged and could be used for traceability, trending or product development.

The monitoring techniques in accordance with embodiments of the present invention have been primarily described with reference to the delivery of bipolar stimulation to detect various adverse events. It is to be appreciated that other embodiments of the monitoring techniques may use multipolar stimulation patterns (e.g., current steering, current/voltage shaping/focussing, etc.) to detect adverse events The monitoring techniques presented herein may provide one or more benefits to recipients, surgeons, or other users. In particular, the monitoring techniques may provide surgeons with a method for determining the state of the stimulating at the time the insertion is performed. This allows the insertion to be corrected immediately if an adverse event has occurred. Confirming the physical state of the stimulating assembly during surgery also reduces the need for post-operative imaging. This translates to cost and time benefits for recipients and hospitals, and reduces recipient exposure to radiation, which is typically associated with current post-operative imaging techniques.

Preventing the occurrence of an adverse event also reduces the risk of trauma inflicted on the soft tissue structures of the cochlea. Furthermore, monitoring stimulating assembly insertion in real-time and being able to respond accordingly to adverse events also offers improved confidence in the quality of the insertion. This reduces the need for revision surgery, improves the hearing performance outcomes of our recipients and ultimately provides recipients with a better, smoother cochlear implant experience. In addition, the proposed invention enables consistent insertions to be performed across all recipients, making the insertion more repeatable regardless of the surgeon's level of experience and training.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
at least partially inserting a stimulating assembly into a cochlea of a recipient of an implantable medical device, wherein the stimulating assembly comprises a plurality of electrodes;
successively sourcing current via at least a subset of the plurality of electrodes;
in response to each sourced current via one of the plurality of electrodes, sinking the sourced current via at least one extra-cochlear electrode;
in response to each sourced current, disconnecting other electrodes of the plurality of electrodes that are not used for sourcing the current;
in response to each sourced current via the one of the plurality of electrodes, measuring a voltage at a plurality of the other electrodes of the plurality of electrodes while the other electrodes of the plurality of electrodes are disconnected;
collecting the voltages measured at the other of the plurality of electrodes of the stimulating assembly obtained in response to each sourced current to generate a plurality of voltage sets; and
analyzing relative magnitudes of the voltages within the plurality of voltage sets to detect the at least one of a fold or a buckle in the stimulating assembly.

2. The method of claim 1, wherein measuring the voltage at the plurality of the other electrodes of the plurality of electrodes comprises:
contemporaneously measuring the voltage at each of the plurality of the other electrodes.

3. The method of claim 1, wherein measuring the voltage at the plurality of the other electrodes of the plurality of electrodes comprises:
successively measuring the voltage at each of the plurality of the other electrodes.

4. The method of claim 1, wherein analyzing the relative magnitudes of the voltages within the plurality of voltage sets to detect the at least one of a fold or buckle in the stimulating assembly further comprises:
analyzing the relative magnitudes of the voltages to determine a location of the at least one of a fold or buckle the stimulating assembly.

5. The method of claim 1, wherein analyzing the relative magnitudes of the voltages within the plurality of voltage sets to detect the at least one of a fold or buckle in the stimulating assembly further comprises:
detecting a global maximum and a local maximum in the relative magnitudes of the voltages indicative of a presence of a fold in the stimulating assembly.

6. The method of claim 1, further comprising:
generating feedback to a user that indicates a presence of the at least one of a fold or buckle in the stimulating assembly.

7. The method of claim 6, wherein generating feedback to a user that indicates the presence of the at least one of a fold or buckle in the stimulating assembly comprises:
displaying an image of an estimated shape of the stimulating assembly at a display screen.

8. The method of claim 6, wherein generating feedback to a user that indicates the presence of the at least one of a fold or buckle in the stimulating assembly comprises:
providing an audible cue indicating the presence of the at least one of a fold or buckle in the stimulating assembly.

9. The method of claim 6, wherein generating feedback to a user that indicates the presence of the at least one of a fold or buckle in the stimulating assembly comprises:
providing a tactile cue indicating the presence of the at least one of a fold or buckle in the stimulating assembly.

10. The method of claim 1, further comprising:
determining, based on the relative magnitudes of the voltages within the plurality of voltage sets, a relative proximity of each electrode of the stimulating assembly to one another; and
estimating a shape of the stimulating assembly based on the relative proximity of each electrode of the stimulating assembly to one another.

11. The method of claim 1, further comprising:
displaying an image of an estimated shape of the stimulating assembly at a display screen.

12. The method of claim 1, wherein analyzing the relative magnitudes of the voltages comprises:

analyzing the relative magnitudes of the voltages to determine a proximity of the one of the plurality of electrodes that sourced the current to one of the other electrodes of the plurality of electrodes that measured the voltage.

13. A system comprising:
a stimulating assembly configured to be at least partially inserted into a cochlea of a recipient of an implantable medical device, wherein the stimulating assembly comprises a plurality of electrodes; and
an event detection processor configured to:
successively source current via at least a subset of the plurality of electrodes;
in response to each sourced current via one of the plurality of electrodes, sink the sourced current via at least one extra-cochlear electrode;
in response to each sourced current, disconnect other electrodes of the plurality of electrodes that are not used for sourcing the current;
in response to each sourced current via the one of the plurality of electrodes, measure a voltage at a plurality of the other electrodes of the plurality of electrodes while the other electrodes of the plurality of electrodes are disconnected;
collect the voltages measured at the other of the plurality of electrodes of the stimulating assembly obtained in response to each sourced current to generate a plurality of voltage sets; and
analyze relative magnitudes of the voltages within the plurality of voltage sets to detect the at least one of a fold or a buckle in the stimulating assembly.

14. The system of claim 13, wherein, when measuring the voltage at the plurality of the other electrodes of the plurality of electrodes, the event detection processor is further configured to:
contemporaneously measure the voltage at each of the plurality of the other electrodes.

15. The system of claim 13, wherein, when measuring the voltage at the plurality of the other electrodes of the plurality of electrodes, the event detection processor is further configured to:
successively measure the voltage at each of the plurality of the other electrodes.

16. The system of claim 13, wherein, when analyzing the relative magnitudes of the voltages within the plurality of voltage sets to detect the at least one of a fold or buckle in the stimulating assembly further, the event detection processor is further configured to:
analyze the relative magnitudes of the voltages to determine a location of the at least one of a fold or buckle the stimulating assembly.

17. The system of claim 13, wherein, when analyzing the relative magnitudes of the voltages within the plurality of voltage sets to detect the at least one of a fold or buckle in the stimulating assembly further, the event detection processor is further configured to:
detect a global maximum and a local maximum in the relative magnitudes of the voltages indicative of a presence of a fold in the stimulating assembly.

18. The system of claim 13, wherein the event detection processor is further configured to:
generate feedback to a user that indicates a presence of the at least one of a fold or buckle in the stimulating assembly.

19. The system of claim 18, wherein, when generating feedback to a user that indicates the presence of the at least one of a fold or buckle in the stimulating assembly, the event detection processor is further configured to:
generate an audible cue indicating the presence of the at least one of a fold or buckle in the stimulating assembly.

20. The system of claim 18, wherein, when generating feedback to a user that indicates the presence of the at least one of a fold or buckle in the stimulating assembly, the event detection processor is further configured to:
generate a tactile cue indicating the presence of the at least one of a fold or buckle in the stimulating assembly.

21. The system of claim 18, wherein, when generating feedback to a user that indicates the presence of the at least one of a fold or buckle in the stimulating assembly, the event detection processor is further configured to:
display an image of an estimated shape of the stimulating assembly at a display screen.

22. The system of claim 13, wherein the event detection processor is further configured to:
determine, based on the relative magnitudes of the voltages within the plurality of voltage sets, a relative proximity of each electrode of the stimulating assembly to one another; and
estimate a shape of the stimulating assembly based on the relative proximity of each electrode of the stimulating assembly to one another.

23. The system of claim 13, wherein the event detection processor is further configured to:
display an image of an estimated shape of the stimulating assembly at a display screen.

24. The system of claim 13, wherein, when analyzing the relative magnitudes of the voltages, the event detection processor is further configured to:
analyze the relative magnitudes of the voltages to determine a proximity of the one of the plurality of electrodes that sourced the current to one of the other electrodes of the plurality of electrodes that measured the voltage.

* * * * *